United States Patent
Chen et al.

(10) Patent No.: US 12,332,388 B2
(45) Date of Patent: Jun. 17, 2025

(54) METHOD FOR DETERMINING $^{224}$Ra IN SEDIMENT BY USING PULSE IONIZATION CHAMBER EMANOMETER

(71) Applicants: First Institute of Oceanography, Ministry of Natural Resources, Qingdao (CN); Ocean University of China, Qingdao (CN); Shandong Marine Resource and Environment Research Institute, Yantai (CN)

(72) Inventors: Guangquan Chen, Qingdao (CN); Wen Liu, Qingdao (CN); Shibin Zhao, Qingdao (CN); Chunqian Li, Qingdao (CN); Jinjia Guo, Qingdao (CN); Yancheng Wang, Qingdao (CN); Bochao Xu, Qingdao (CN); Xiaofei Yin, Qingdao (CN); Shan Sun, Yantai (CN)

(73) Assignees: First Institute of Oceanography, Ministry of Natural Resources, Qingdao (CN); Ocean University of China, Qingdao (CN); Shandong Marine Resource and Environment Research Institute, Yantai (CN)

( * ) Notice: Subject to any disclaimer, the term of this patent is extended or adjusted under 35 U.S.C. 154(b) by 384 days.

(21) Appl. No.: 17/868,889

(22) Filed: Jul. 20, 2022

(65) Prior Publication Data
US 2023/0375725 A1  Nov. 23, 2023

(30) Foreign Application Priority Data
May 18, 2022  (CN) .......................... 202210549978.8

(51) Int. Cl.
*G01T 1/167* (2006.01)
*G01N 33/24* (2006.01)
(Continued)

(52) U.S. Cl.
CPC ............. *G01T 1/178* (2013.01); *G01N 33/24* (2013.01); *G01T 1/167* (2013.01); *G01T 1/185* (2013.01); *G01N 33/0093* (2024.05)

(58) Field of Classification Search
CPC .......... G01T 1/167; G01T 1/178; G01T 1/185
(Continued)

(56) References Cited

U.S. PATENT DOCUMENTS 1,395,120 A  * 10/1921 Kunkle .................... G21G 4/10
                                                                 250/336.1
4,871,914 A  * 10/1989 Simon ..................... G01T 1/247
                                                                250/DIG. 2
(Continued)

OTHER PUBLICATIONS

Junhyeong Seo and Guebuem Kim, Rapid and precise measurements of radon in water using a pulsed ionization chamber, Limnol. Oceanogr.: Methods 19, 2021, 245-252. (Year: 2021).*
(Continued)

*Primary Examiner* — Allen C. Ho
(74) *Attorney, Agent, or Firm* — Gerald E. Hespos; Michael J Porco

(57) ABSTRACT

Disclosed is a method for determining $^{224}$Ra in a sediment by using a pulse ionization chamber emanometer, which belongs to the technical field of analysis and measurement. A pulse ionization chamber emanometer (PIC), a new emanometer, is used. Based on the half-life characteristics of different radon isotopes, one can separate the $^{220}$Rn activity from the total counts by dual counting. The resulting $^{220}$Rn measurement then can be used to determine the $^{224}$Ra activity in sediment according to the principle of secular radioactive equilibrium.

9 Claims, 2 Drawing Sheets

(51) Int. Cl.
*G01T 1/178* (2006.01)
*G01T 1/185* (2006.01)
*G01N 33/00* (2006.01)

(58) Field of Classification Search
USPC ........................................................ 250/255
See application file for complete search history.

(56) References Cited

U.S. PATENT DOCUMENTS

| | | | | |
|---|---|---|---|---|
| 4,960,998 A * | 10/1990 | Peter | ........................ | G01T 1/178 |
| | | | | 250/370.03 |
| 5,047,634 A * | 9/1991 | Guelin | ........................ | G01T 7/04 |
| | | | | 250/DIG. 2 |
| 5,107,108 A * | 4/1992 | Ramsey | ................... | G01T 1/178 |
| | | | | 250/DIG. 2 |
| 5,128,540 A * | 7/1992 | Stieff | ........................ | G01T 1/14 |
| | | | | 250/DIG. 2 |
| 5,210,419 A * | 5/1993 | Buheitel | ................. | G01T 1/178 |
| | | | | 250/362 |
| 5,235,190 A * | 8/1993 | Tucker | ..................... | G01T 7/04 |
| | | | | 250/435 |
| 6,768,116 B1 * | 7/2004 | Berman | .................. | G01T 1/178 |
| | | | | 250/374 |
| 6,847,033 B2 * | 1/2005 | Freyer | .................... | B01D 53/22 |
| | | | | 250/435 |
| 8,459,096 B2 * | 6/2013 | Chyi | ........................ | G01T 1/178 |
| | | | | 73/19.01 |
| 10,132,936 B2 * | 11/2018 | Ko | ............................ | G01T 7/00 |
| 10,214,482 B2 * | 2/2019 | Ingram | .................. | C10L 3/103 |
| 10,279,309 B2 * | 5/2019 | Ingram | .............. | B01D 53/1493 |
| 11,041,964 B2 * | 6/2021 | Eguchi | ...................... | G01T 1/17 |
| 11,169,281 B2 * | 11/2021 | Ko | ........................... | G01T 1/185 |
| 11,173,446 B2 * | 11/2021 | Ingram | ............. | B01D 53/1425 |
| 12,013,500 B2 * | 6/2024 | Ko | ........................ | H01J 47/026 |

OTHER PUBLICATIONS

Marian Romeo Calin and Mihaela Antonina Calin, System for air 222Rn activity concentration measurements based on ion-pulse ionization chamber detector, J Radioanal Nucl Chem (2011) 288:109-114. (Year: 2011).*

* cited by examiner

METHOD FOR DETERMINING $^{224}$Ra IN SEDIMENT BY USING PULSE IONIZATION CHAMBER EMANOMETER

CROSS REFERENCE TO RELATED APPLICATION

This patent application claims the benefit and priority of Chinese Patent Application No. 202210549978.8, entitled "Method for determining $^{224}$Ra in sediment by using pulse ionization chamber emanometer" filed on May 18, 2022, the disclosure of which is incorporated by reference herein in its entirety as part of the present application.

TECHNICAL FIELD

The present disclosure relates to the technical field of analysis and measurement, particularly to a method for determining $^{224}$Ra in a sediment by using a pulse ionization chamber emanometer.

BACKGROUND ART

Radium isotopes with short half-life ($^{224}$Ra, $T_{1/2}$=3.66 days) are suitable for studying oceanographic processes on short time scales (several days to several weeks). Some researchers have used $^{224}$Ra to study $^{224}$Ra/$^{228}$Th disequilibrium phenomenon in marine sediments, and then quantified the exchange flux of trace metals, nutrients and dissolved organic carbon at the sediment-water interface by the $^{224}$Ra/$^{228}$Th disequilibrium method. At present, the conventionally used method for determining $^{224}$Ra in sediments is the Radium Delayed Coincidence Counter (RaDeCC) method. The method allows for accurately and rapidly detecting the activity of $^{224}$Ra in sediments, with a measurement accuracy of ±(5%-7%) and a repeatability of ±5%. However, since this method requires helium gas and 220/110 V line voltage, it is unsuitable for remote study sites without a power supply or access to helium.

SUMMARY

An object of the present disclosure is to provide a method for determining $^{224}$Ra in sediment by using a pulse ionization chamber (PIC) emanometer. The method according to the present disclosure does not need to carry helium gas cylinders, has low testing cost and high testing efficiency, and is convenient for on-site measuring.

To achieve the above object, the present disclosure provides the following technical solutions:

The present disclosure provides a method for determining $^{224}$Ra in sediment by using a pulse ionization chamber emanometer, comprising steps of (1) placing a sediment standard sample of $^{224}$Ra in a sample tray, connecting the sample tray with an air pump and the pulse ionization chamber emanometer, to form an enclosed test system;

turning on the air pump and circulating gas in the test system for at least 5 minutes, such that a radioactive equilibrium between $^{220}$Rn gas released from the sediment standard sample and $^{224}$Ra in the sediment standard sample is reached, and performing a first continuous measurement for an activity of Rn in the test system, which would obtain a sum of counting rates of $^{222}$Rn and $^{220}$Rn, represented by $C_1$ in cpm;

turning off the air pump, closing inlet valve(s) and outlet valve(s) of the pulse ionization chamber emanometer, and leaving the pulse ionization chamber emanometer to stand for at least 5 minutes, such that $^{220}$Rn in the pulse ionization chamber emanometer completely decays and disappears, and performing a second continuous measurement for an activity of Rn in the pulse ionization chamber emanometer, which would obtain a counting rate of $^{222}$Rn, represented by $C_2$ in cpm;

calculating a counting rate of $^{224}$Ra in the sediment standard sample according to equation 1;

$$C_p = C_d = C_1 - C_2 \qquad \text{equation 1,}$$

in equation 1, $C_p$ represents the counting rate of parent isotope $^{224}$Ra in the sediment standard sample, and Ca represents the counting rate of daughter isotope $^{220}$Rn in the sediment standard sample;

(2) repeating step (1) by using different sediment standard samples with a $^{224}$Ra activity gradient to obtain counting rates of $^{224}$Ra in different sediment standard samples with a $^{224}$Ra activity gradient;

plotting a standard curve of activities of $^{224}$Ra versus counting rates, in which the counting rates of $^{224}$Ra in the different sediment standard samples are set as ordinate, and $^{224}$Ra activities in the different sediment standard samples are set as abscissa; and (3) performing a measurement on a sediment sample according to step (1) to obtain a counting rate of $^{224}$Ra (cpm), and calculating the $^{224}$Ra activity of the sediment sample according to the standard curve obtained in step (2).

In some embodiments, the sediment sample and the sediment standard samples are in same type.

In some embodiments, an air flow rate provide by the air pump is 0.5-3 L/min.

In some embodiments, each of the sediment sample to be tested and the sediment standard samples independently has a moister content of 0-70 wt %.

In some embodiments, the first continuous measurement is performed for 0.5-6 hours.

In some embodiments, the second continuous measurement is performed for 0.5-4 hours.

In some embodiments, the method further comprises calculating a relative standard deviation of the activity of $^{224}$Ra in the sediment sample to be tested after step (3).

In some embodiments, calculating a relative standard deviation of the activity of $^{224}$Ra in the sediment sample to be tested is performed by a process comprising calculating a standard deviation of the sum of counting rates of $^{222}$Rn and $^{220}$Rn obtained from the first continuous measurement according to equation 2 and equation 3, $$\sigma_1 = \frac{\sqrt{N_1}}{N_1} \times C_1; \qquad \text{equation 2}$$

$$N_1 = C_1 \times T_1; \qquad \text{equation 3}$$

in equations 2 and 3, al represents the standard deviation of the sum of counting rates of $^{222}$Rn and $^{220}$Rn obtained from the first continuous measurement, in cpm; $N_1$ represents a counting value in the first continuous measurement, in counts; $T_1$ represents time for the first continuous measurement, in minute;

calculating a standard deviation of the counting rate of $^{222}$Rn obtained from the second continuous measurement according to equation 4 and equation 5, $$\sigma_2 = \frac{\sqrt{N_2}}{N_2} \times C_2; \qquad \text{equation 4}$$

$$N_2 = C_2 \times T_2; \qquad \text{equation 5}$$

in equations 4 and 5, $\sigma_2$ represents the standard deviation of the counting rate of $^{222}$Rn obtained from the second continuous measurement, in cpm; $N_2$ represents a counting value in the second continuous measurement, in counts; $T_2$ represents time for the second continuous measurement, in minute; and calculating the relative standard deviation of the activity of $^{224}$Ra according to equation 6, represented by $\delta$ in equation 6, $$\delta = \frac{\sqrt{\sigma_1^2 + \sigma_2^2}}{C_1 - C_2} \times 100\%. \qquad \text{equation 6}$$

In some embodiments, each of the sediment sample to be tested and the sediment standard samples independently has a mass of 1-60 g.

In the method according to the present disclosure, a new emanometer, i.e. a pulse ionization chamber emanometer (PIC) is used, and based on the half-life characteristics of different radon isotopes, one can separate the $^{220}$Rn activity from the total counts by dual counting. The resulting $^{220}$Rn measurement then can be used to determine the $^{224}$Ra activity. The method according to the present disclosure does not need to carry helium gas cylinders, has low measurement cost and high testing efficiency, and is convenient for on-site measuring.

According to the present disclosure, the measurement principle is as follows.

The α-decay of $^{224}$Ra produces a gaseous daughter $^{220}$Rn. Since the half-life of $^{224}$Ra ($T_{1/2}$=3.66 days) is much longer than that of its daughter $^{220}$Rn ($T_{1/2}$=55.6 s), according to the principle of secular radioactive equilibrium, the activity of $^{224}$Ra is the same as that of $^{220}$Rn after five-fold time of the half-life of $^{220}$Rn (i.e., five minutes). Therefore, the content of $^{224}$Ra in a sediment could be indirectly determined by determining the gaseous daughter $^{220}$Rn of $^{224}$Ra by using a PIC emanometer.

It should be noted that the result measured by PIC is the sum of the radon isotopes in the gas. The parent nuclide of the radon isotopes is the radium isotope (Ra). There are four natural radioactive radium isotopes, namely $^{228}$Ra ($T_{1/2}$=5.75 years), $^{226}$Ra ($T_{1/2}$=1620 years), $^{224}$Ra ($T_{1/2}$=3.66 days) and $^{223}$Ra ($T_{1/2}$=11.4 days), and three types of Rn isotopes would be produced when they decay, namely $^{222}$Rn ($T_{1/2}$=3.83 days), $^{220}$Rn ($T_{1/2}$=55.6 s) and $^{219}$Rn ($T_{1/2}$=3.96 s). Since the object measured in the ionization chamber are positive and negative charges generated by ionizing air with alpha particles, the three nuclides $^{222}$Rn, $^{220}$Rn and 219Rn could not be directly distinguished by the PIC. In order to obtain the activity of $^{220}$Rn in the gas alone, the following technical solutions are designed in the present disclosure.

First, since the content of $^{223}$Ra in the sediment is extremely low and the half-life of $^{219}$Rn is very short, the influence of $^{219}$Rn on the $^{220}$Rn measurement in the sediment could be ignored during the measurement.

Secondly, since $^{222}$Rn ($T_{1/2}$=3.83 days) and $^{220}$Rn ($T_{1/2}$=55.6 s) are largely different in half-life, and the half-life of $^{220}$Rn is relatively shorter, the sum of counting rates of $^{222}$Rn and $^{220}$Rn (represented by $C_1$) could be measured first. Thereafter inlet valve(s) and outlet valve(s) of the PIC are closed (equivalent to removing the sample Rn source), and the entire PIC measurement system is left to stand for 5 minutes. After the $^{220}$Rn in the ionization chamber completely decays, the result measured by the PIC is just the counting rate of $^{222}$Rn (represented by $C_2$) in the system. The self decay of $^{222}$Rn could be ignored during the whole measurement, and thus the difference between the two measurement results is the counting rate of $^{220}$Rn (represented by $C_d$), and the counting rate $^{224}$Ra in the sediment sample (represented by $C_p$) is equal to the counting rate of the daughter $^{220}$Rn (represented by $C_d$), which could be summarized as follows:

$$C_p = C_d = C_1 - C_2.$$

DETAILED DESCRIPTION OF THE EMBODIMENTS

The present disclosure provides a method for determining $^{224}$Ra in a sediment by using a pulse ionization chamber emanometer, comprising steps of (1) placing a sediment standard sample of $^{224}$Ra in a sample tray, connecting the sample tray with an air pump and the pulse ionization chamber emanometer, to form an enclosed test system;

turning on the air pump and circulating gas in the test system for at least 5 minutes, such that a radioactive equilibrium between $^{220}$Rn gas released from the sediment standard sample and $^{224}$Ra in the sediment standard sample is reached, and performing a first continuous measurement for an activity of Rn in the test system, to obtain a sum of counting rates of $^{222}$Rn and $^{220}$Rn, represented by $C_1$ in cpm;

turning off the air pump, closing inlet valve(s) and outlet valve(s) of the pulse ionization chamber emanometer, and leaving the pulse ionization chamber emanometer to stand for at least 5 minutes, such that $^{220}$Rn in the pulse ionization chamber emanometer completely decays and disappears, and performing a second continuous measurement for an activity of Rn in the pulse ionization chamber emanometer, to obtain a counting rate of $^{222}$Rn, represented by $C_2$ in cpm;

calculating a counting rate of $^{224}$Ra in the sediment standard sample according to equation 1;

$$C_p = C_d = C_1 - C_2 \qquad \text{equation 1,}$$

in equation 1, $C_p$ represents the counting rate of $^{224}$Ra in the sediment standard sample, and Ca represents the counting rate of $^{220}$Rn in the sediment standard sample;

(2) repeating step (1) by using different sediment standard samples with a $^{224}$Ra activity gradient to obtain counting rates of $^{224}$Ra in different sediment standard samples with a $^{224}$Ra activity gradient;

plotting a standard curve of activities of $^{224}$Ra versus counting rates, in which the counting rates of $^{224}$Ra in the different sediment standard samples are set as ordinate, and $^{224}$Ra activities in the different sediment standard samples are set as abscissa; and (3) performing a measurement on a sediment sample according to step (1) to obtain a counting rate of $^{224}$Ra (cm) and calculating the $^{224}$Ra activity of the sediment sample according to the standard curve obtained in step (2).

Figure 1:
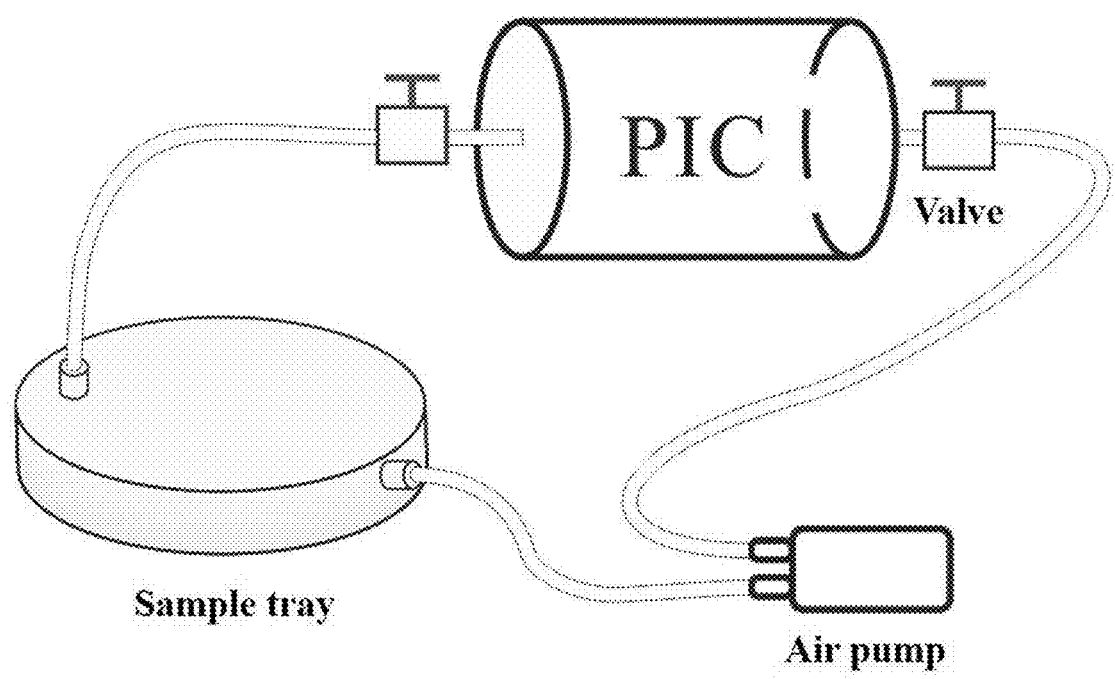
FIG. 1 shows the schematic diagram of the device used in some embodiments of the present disclosure.
Figure 2:
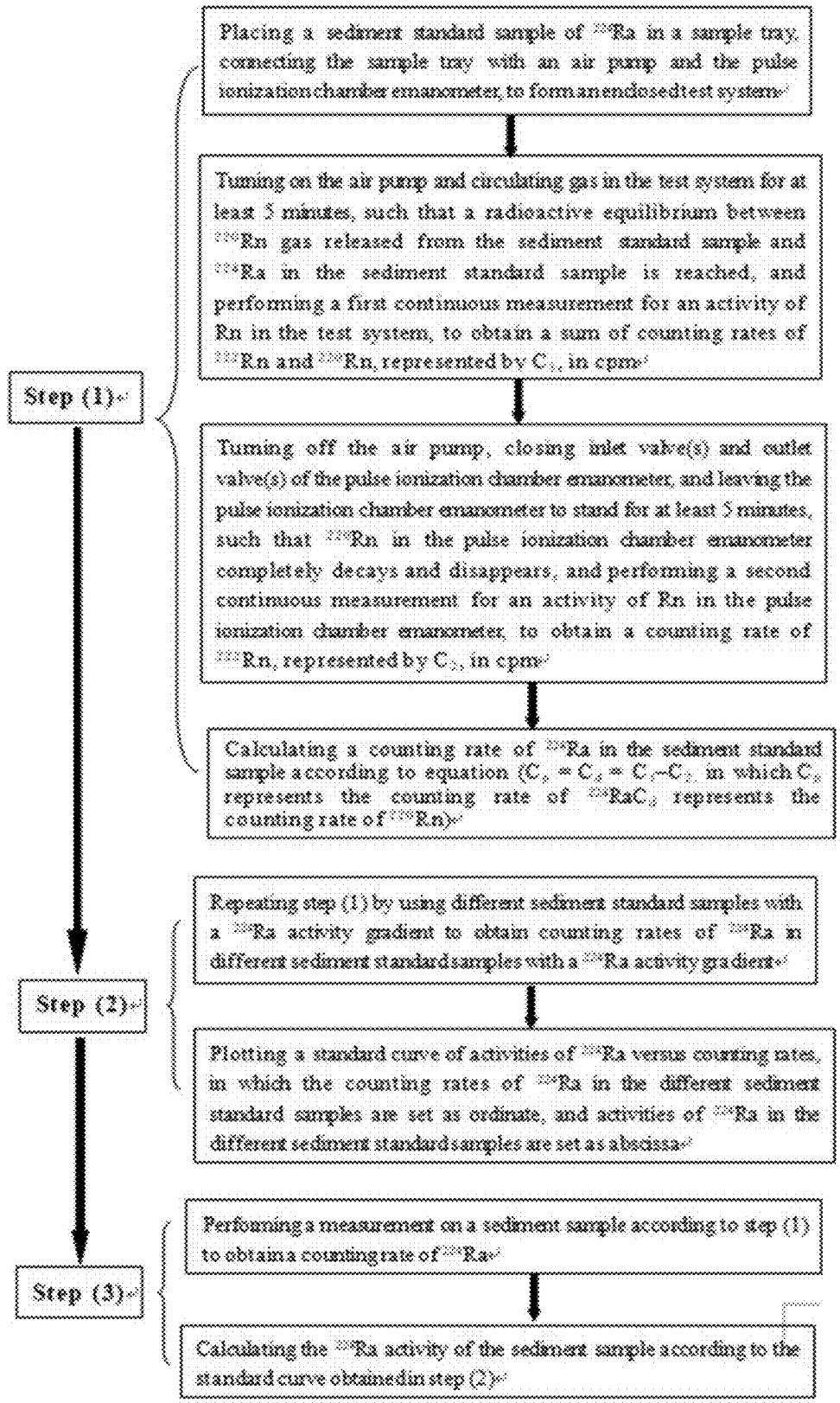
FIG. 2 shows a schematic flow chart of the method for determining $^{224}$Ra in a sediment according to some embodiments of the present disclosure.

As shown in FIG. 1, in the method according to the present disclosure, the sediment standard sample of $^{224}$Ra is first placed in the sample tray, and the sample tray is connected with the air pump and the pulse ionization chamber emanometer, to form an enclosed test system.

In the present disclosure, there is no special type limitation on the pulse ionization chamber (PIC) emanometer, and any PIC well known in the art may be used. In the present disclosure, there is no special requirements on the connection method of the sample tray, the air pump and the pulse ionization chamber emanometer, and the connection method well known in the art may be adopted, which is common knowledge in the art. In the present disclosure, there is no special requirement on the type of the sediment standard sample, for example clay and silt. In some embodiments of the present disclosure, the sediment standard sample has a moisture content of 0-70 wt %. Those skilled in the art could select an appropriate moisture content according to the particle size of the sediment standard sample. In some embodiments of the present disclosure, the sediment standard sample has a mass of 1-60 g, preferably 10-50 g, and further preferably 20-40 g.

According to the present disclosure, after the enclosed test system is formed, the air pump is turn on, and the gas in the test system is circulated for at least 5 minutes, such that a radioactive equilibrium between $^{220}$Rn gas released from the sediment standard sample and $^{224}$Ra in the sediment standard sample is reached, and a first continuous measurement is performed for an activity of Rn in the test system, to obtain a sum of counting rates of $^{222}$Rn and $^{220}$Rn, represented by $C_1$, in cpm.

In some embodiments of the present disclosure, the air pump is run to provide a constant flow rate of 0.5 to 3.0 L/min, and preferably 1.0 to 2.0 L/min.

The α decay of $^{224}$Ra produces a gaseous daughter $^{220}$Rn. Since the half-life of $^{224}$Ra ($T_{1/2}$=3.66 days) is much longer than that of its daughter $^{220}$Rn ($T_{1/2}$=55.6 s), According to the principle of secular radioactive equilibrium, the activity of $^{224}$Ra is the same as that of $^{220}$Rn after five-fold time of the half-life of $^{220}$Rn (i.e., five minutes). There are four natural radioactive radium isotopes in nature, namely $^{228}$Ra ($T_{1/2}$=5.75 years), $^{226}$Ra ($T_{1/2}$=1620 years), $^{224}$Ra ($T_{1/2}$=3.66 days) and $^{223}$Ra ($T_{1/2}$=11.4 days), and three types of Rn isotopes would be produced when they decay, namely $^{222}$Rn ($T_{1/2}$=3.83 days), $^{220}$Rn ($T_{1/2}$=55.6 s) and $^{219}$Rn ($T_{1/2}$=3.96 s). Since the object measured in the ionization chamber are positive and negative charges generated by ionizing air with alpha particles, the three nuclides $^{222}$Rn, $^{220}$Rn and $^{219}$Rn could not be directly distinguished by the PIC. Therefore, in the first continuous measurement, the result measured by PIC is the sum of the radon isotopes in the gas ($^{222}$Rn, $^{220}$Rn and $^{219}$Rn). Since the content of $^{223}$Ra in the sediment is extremely low and the half-life of $^{219}$Rn is very short, the influence of $^{219}$Rn on the $^{220}$Rn measurement in the sediment could be ignored during the measurement. Therefore, the result obtained in the first continuous measurement is the sum of the activities (counting rates) of $^{222}$Rn and $^{220}$Rn.

In the present disclosure, the counting rate is expressed in unit of cpm, i.e., counts per minute, which is the number of decays of radioactive isotopes per minute observed by the instrument, which corresponding to the activity of the radioactive element at the corresponding stage of the measurement by the PIC emanometer.

In the present disclosure, there is no special requirements on the upper limit of the time for the gas circulation.

In some embodiments of the present disclosure, the first continuous measurement is performed for 0.5 to 6 hours, and preferably 2 to 4 hours. A longer time for the first continuous measurement would result in a higher counting value, thereby causing a smaller measurement error at this stage. The time for the first continuous measurement could be selected according to the measurement error requirement. The calculation of the error will be described in detail below.

According to the present disclosure, after obtaining the sum of counting rates of $^{222}$Rn and $^{220}$Rn ($C_1$), inlet valve(s) and outlet valve(s) of the pulse ionization chamber emanometer are closed, and the pulse ionization chamber emanometer is left to stand for at least 5 minutes such that the $^{220}$Rn in the pulse ionization chamber emanometer completely decays and disappears, and a second continuous measurement is performed for an activity of Rn in the pulse ionization chamber emanometer, to obtain a counting rate of $^{222}$Rn, represented by $C_2$, in cpm.

In some embodiments of the present disclosure, leaving the pulse ionization chamber emanometer to stand is performed for 5 to 10 minutes.

In some embodiments of the present disclosure, the second continuous measurement is performed for 0.5 to 4 hours, and preferably 1 to 3 hours. A longer time for the second continuous measurement results in a higher counting value, thereby causing a smaller measurement error at this stage. The time for the second continuous measurement could be chosen according to the measurement error requirement. The calculation of the error will be described in detail below.

According to the present disclosure, after obtaining the sum of counting rates of $^{222}$Rn and $^{220}$Rn ($C_1$) and the counting rate of $^{222}$Rn ($C_2$), the counting rate of $^{224}$Ra in the sediment standard sample is calculated according to equation 1, $$C_p = C_d = C_1 - C_2 \qquad \text{equation 1,}$$

in equation 1, $C_p$ represents the counting rate of $^{224}$Ra in the sediment standard sample, and $C_d$ represents the counting rate of $^{220}$Rn in the sediment standard sample.

According to the present disclosure, the above steps are repeated by using different sediment standard samples with a $^{224}$Ra activity gradient to obtain counting rates of $^{224}$Ra in different sediment standard samples with a $^{224}$Ra activity gradient. A standard curve of activities of $^{224}$Ra versus counting rates is plotted, in which the counting rates (cpm) of $^{224}$Ra in the different sediment standard samples are set as ordinate, and activities of $^{224}$Ra in the different sediment standard samples are set as abscissa.

In the present disclosure, there is no special requirements on the progress for plotting the standard curve. According to the present disclosure, after plotting the standard curve, a linear equation of activities of $^{224}$Ra versus counting rates and a correlation coefficient ($R^2$) are obtained, and a correlation coefficient ($R^2$) much closer to 1 indicates a higher accuracy of the measurement method according to the present disclosure. In some embodiments of the present disclosure, the linear equation is shown in equation 7:

$$C_1 - C_2 = kA_{standard} + b \qquad \text{equation 7,}$$

in equation 7, $(C_1-C_2)$ equals to the counting rate of $^{224}$Ra, $A_{standard}$ represents the activity of $^{224}$Ra in the standard sample, k represents the instrument efficiency, and b represents the background value of the $^{224}$Ra in the sediment sample.

According to the present disclosure, after obtaining the standard curve of activities of $^{224}$Ra versus counting rates, a measurement is performed on the sediment sample to be tested according to the above-mentioned steps, to obtain the counting rate of $^{224}$Ra in the sediment sample to be tested, and the activity of $^{224}$Ra in the sediment sample to be tested is calculated according to the standard curve of activities of $^{224}$Ra versus counting rates.

In some embodiments of the present disclosure, the sediment sample to be tested and the sediment standard samples are in same type. For example, if the sediment standard sample is a silty sediment, the sample to be tested is also a silty sediment.

In some embodiments, the activity of $^{224}$Ra in the sediment sample to be tested is calculated according to the linear equation which corresponds to the standard curve, and the activity of $^{224}$Ra calculated is the theoretically calculated activity. In the present disclosure, the activity of $^{224}$Ra in the sediment sample to be tested ($C_{theory}$) is calculated according to equation 8, $$C_{theory}=(C_1-C_2)/k \quad \text{equation 8.}$$

In order to ensure the accuracy of the measurement, the method according to the present disclosure further comprises calculating a relative standard deviation of the activity of $^{224}$Ra in the sediment sample to be tested.

In some embodiments of the present disclosure, calculating the relative standard deviation of the activity of $^{224}$Ra in the sediment sample to be tested is performed by a process comprises the following steps:

calculating a standard deviation of the sum of counting rates of $^{222}$Rn and $^{220}$Rn obtained from the first continuous measurement according to equation 2 and equation 3, $$\sigma_1 = \frac{\sqrt{N_1}}{N_1} \times C_1, \quad \text{equation 2}$$

$$N_1 = C_1 \times T_1, \quad \text{equation 3}$$

in equations 2 and 3, $\sigma_1$ represents the standard deviation of the sum of counting rates of $^{222}$Rn and $^{220}$Rn obtained from the first continuous measurement, in cpm; $N_1$ represents a counting value in the first continuous measurement, in counts; $T_1$ represents time for the first continuous measurement, in minute;

calculating a standard deviation of the counting rate of $^{222}$Rn obtained from the second continuous measurement according to equation 4 and equation 5, $$\sigma_2 = \frac{\sqrt{N_2}}{N_2} \times C_2, \quad \text{equation 4}$$

$$N_2 = C_2 \times T_2; \quad \text{equation 5}$$

in equations 4 and 5, $\sigma_2$ represents the standard deviation of the counting rate of $^{222}$Rn obtained from the second continuous measurement, in cpm; $N_2$ represents a counting value in the second continuous measurement, in counts; $T_2$ represents time for the second continuous measurement, in minute; and calculating the relative standard deviation of the activity of $^{224}$Ra according to equation 6, represented by $\delta$ in equation 6, $$\delta = \frac{\sqrt{\sigma_1^2 + \sigma_2^2}}{C_1 - C_2} \times 100\%. \quad \text{equation 6}$$

In the present disclosure, the relationship between the actual activity of $^{224}$Ra in the sediment sample to be tested and the theoretical activity therefore is represented by $C_{actual}=C_{theory}\times(1\pm\delta)$.

The method for determining $^{224}$Ra in a sediment by using a pulse ionization chamber emanometer according to the present disclosure will be described in detail below in conjunction with the examples, but they should not be construed as limiting the scope of the present disclosure.

Example 1

Six standard samples of silty sediments with a known $^{224}$Ra activity gradient was provided. An experimental device as shown in Figure was used. The moister contents of the standard samples of sediments were adjusted to 30 wt %. An air pump was turned on, and the flow rate was adjusted to 1 L/min. The gas was circulated in the system for 5 minutes, such that a radioactive equilibrium between $^{220}$Rn gas released from the sediment standard sample and $^{224}$Ra in the sediment standard sample was reached, and a first continuous measurement for Rn in the test system was performed for 2 hours, obtaining the sum of the counting rates of $^{222}$Rn and $^{220}$Rn (i.e. $C_1$). The air pump was turned off. The inlet valve(s) and outlet valve(s) of the PIC were closed, and the PIC was left to stand for at least 5 minutes, such that the $^{220}$Rn in the PIC completely decayed and disappeared. A second continuous measurement for the activity of Rn in the PIC was performed for 2 hours, obtaining the counting rate of the $^{222}$Rn ($C_2$). The difference between the two measurement results (i.e. $C_1-C_2$) was the counting rate of $^{220}$Rn in the system, i.e. the counting rate of $^{224}$Ra. A standard curve of activities of $^{224}$Ra versus counting rates was plotted, in which the counting rates of $^{224}$Ra in the different sediment standard samples are set as ordinate, and activities of $^{224}$Ra in the different sediment standard samples are set as abscissa. The standard curve was fitted, obtaining a linear equation and $R^2$ value, the linear equation being shown as equation 9, $$C_1-C_2=0.2A_{standard}+1.6 \quad \text{equation 9.}$$

20 g of silty sediment to be tested was provided and placed into a sample tray, and subjected to a measurement according to the same procedure and conditions as the sediment standard samples. The moisture content of the sediment was adjusted the same as the standard samples, i.e., 30 wt %. The air pump was turned on, and the flow rate was adjusted to 1 L/min. The gas in the system was circulated for 5 minutes. A first continuous measurement for Rn in the test system was performed for 2 hours, obtaining a total counting rate of Rn ($C_1$) of 5.0 cpm. The inlet valve(s) and outlet valve(s) of the PIC were closed. The PIC emanometer was left to stand for 5 minutes, such that the $^{220}$Rn in the PIC completely decayed and disappeared. A second continuous measurement was performed for 2 hours for the activity of $^{222}$Rn in the PIC, obtaining the counting rate of $^{222}$Rn ($C_2$)

of 0.8 cpm. The difference between the two measurement results was the counting rate of the $^{220}$Rn in the system, i.e. 5.0 cpm-0.8 cpm=4.2 cpm. Since the $^{224}$Ra in the sediment and the $^{220}$Rn in the system were in a secular radioactive equilibrium, the counting rate of $^{224}$Ra by the instrument was 4.2 cpm. For the silty sediment samples, the standard sample had an efficiency of 0.2 cpm/dpm with $R^2$ larger than 0.99. According to equation 9, the theoretical activity of $^{224}$Ra in the sediment sample was calculated to be 1.05 dpm/g, i.e. 4.2 cpm/0.2 (cpm/dpm)/20 g=1.05 dpm/g.

Error Calculation:

The error of total radon in the first continuous measurement: 5 cpm×120 min=600 counts, the standard deviation of the counting rate ($\sigma_1$) was 0.2 cpm, i.e. $\sigma_1=$ $$\frac{\sqrt{600}}{600} \times 5 = 0.2\ cpm;$$

The error of $^{222}$Rn in the second continuous measurement: 0.8×120 min=96 counts, the standard deviation of the counting rate ($\sigma_2$) was 0.08 cpm, i.e.

$$o2 = \frac{\sqrt{96}}{96} \times 0.8 = 0.08\ cpm;$$

Therefore, the relative standard deviation of $^{224}$Ra ($\delta$) was 5%, i.e.

$$\delta = \frac{\sqrt{0.2^2 + 0.08^2}}{4.2} \times 100\% = 5\%.$$

Therefore, the actual activity of $^{224}$Ra in the sediment sample ($C_{actual}$) was 1.05±0.05 dpm/g, i.e. $C_{actual}$=1.05 dpm/g×(1±0.05)=1.05±0.05 dpm/g.

The above are only the preferred embodiments of the present disclosure. It should be pointed out that for those skilled in the art, without departing from the principles of the present disclosure, several improvements and modifications could be made. And the improvements and modifications shall fall within the scope of the present disclosure.

What is claimed is:

1. A method for determining $^{224}$Ra in a sediment by using a pulse ionization chamber emanometer, comprising steps of:

(1) placing a sediment standard sample of $^{224}$Ra in a sample tray, connecting the sample tray with an air pump and the pulse ionization chamber emanometer, to form an enclosed test system;

turning on the air pump and circulating gases in the enclosed test system for at least 5 minutes, such that a radioactive equilibrium between a $^{220}$Rn gas released from the sediment standard sample and $^{224}$Ra in the sediment standard sample is reached, and performing a first continuous measurement for an activity of Rn in the enclosed test system, to obtain a sum of counting rates of $^{222}$Rn and $^{220}$Rn, represented by $C_1$, in cpm;

turning off the air pump, closing inlet valve(s) and outlet valve(s) of the pulse ionization chamber emanometer, and leaving the pulse ionization chamber emanometer to stand for at least 5 minutes, such that $^{220}$Rn in the pulse ionization chamber emanometer completely decays and disappears, and performing a second continuous measurement for an activity of Rn in the pulse ionization chamber emanometer, to obtain a counting rate of $^{222}$Rn, represented by $C_2$, in cpm; and calculating a counting rate of $^{224}$Ra in the sediment standard sample according to equation 1;

$$C_p = C_d = C_1 - C_2 \qquad \text{equation 1,}$$

in equation 1, $C_p$ represents the counting rate of $^{224}$Ra in the sediment standard sample, and $C_d$ represents the counting rate of $^{220}$Rn in the sediment standard sample;

(2) repeating step (1) by using different sediment standard samples with a $^{224}$Ra activity gradient to obtain counting rates of $^{224}$Ra in the different sediment standard samples with the $^{224}$Ra activity gradient; and plotting a standard curve of activities of $^{224}$Ra versus counting rates of $^{224}$Ra, in which the counting rates of $^{224}$Ra in the different sediment standard samples are set as ordinate, and activities of $^{224}$Ra in the different sediment standard samples are set as abscissa; and (3) performing a measurement on a sediment sample to be tested according to step (1) to obtain a counting rate of $^{224}$Ra in the sediment sample to be tested, and calculating an activity of $^{224}$Ra in the sediment sample to be tested according to the standard curve of activities of $^{224}$Ra versus counting rates of $^{224}$Ra obtained in step (2).

2. The method as claimed in claim 1, wherein the sediment sample to be tested and the different sediment standard samples are in same type.

3. The method as claimed in claim 1, wherein an air flow rate provided by the air pump is in a range of 0.5-3 L/min.

4. The method as claimed in claim 1, wherein the sediment sample to be tested has a moisture content of 0-70 wt % and each of the different sediment standard samples independently has a moisture content of 0-70 wt %.

5. The method as claimed in claim 1, wherein the first continuous measurement for an activity of Rn in the enclosed test system is performed for 0.5 to 6 hours.

6. The method as claimed in claim 1, wherein the second continuous measurement for an activity of Rn in the pulse ionization chamber emanometer is performed for 0.5 to 4 hours.

7. The method as claimed in claim 1, further comprising calculating a relative standard deviation of the activity of $^{224}$Ra in the sediment sample to be tested after step (3).

8. The method as claimed in claim 7, wherein calculating the relative standard deviation of the activity of $^{224}$Ra in the sediment sample to be tested is performed by a process comprising:

calculating a standard deviation of the sum of counting rates of $^{222}$Rn and $^{220}$Rn obtained from the first continuous measurement according to equation 2 and equation 3, $$\sigma_1 = \frac{\sqrt{N_1}}{N_1} \times C_1, \qquad \text{equation 2}$$

$$N_1 = C_1 \times T_1, \qquad \text{equation 3}$$

in equations 2 and 3, $\sigma_1$ represents the standard deviation of the sum of counting rates of $^{222}$Rn and $^{220}$Rn obtained from the first continuous measurement, in cpm; $N_1$ represents a counting value in the first continuous measurement, in counts; $T_1$ represents a time for the first continuous measurement, in minute;

calculating a standard deviation of the counting rate of $^{222}$Rn obtained from the second continuous measurement according to equation 4 and equation 5, $$\sigma 2 = \frac{\sqrt{N_2}}{N_2} \times C_2, \qquad \text{equation 4}$$

$$N_2 = C_2 \times T_2, \qquad \text{equation 5}$$

in equations 4 and 5, $\sigma_2$ represents the standard deviation of the counting rate of $^{222}$Rn obtained from the second continuous measurement, in cpm; $N_2$ represents a counting value in the second continuous measurement, in counts; $T_2$ represents a time for the second continuous measurement, in minute; and calculating, according to equation 6, the relative standard deviation of the activity of $^{224}$Ra in the sediment sample to be tested, the relative standard deviation being represented by $\delta$ in equation 6;

$$\delta = \frac{\sqrt{\sigma_1^2 + \sigma_2^2}}{C_1 - C_2} \times 100\%. \qquad \text{equation 6}$$

9. The method as claimed in claim 1, wherein the sediment sample to be tested has a mass of 1-60 g and each of the different sediment standard samples independently has a mass of 1-60 g.

* * * * *